(12) United States Patent
Ihara et al.

(10) Patent No.: US 8,193,224 B2
(45) Date of Patent: Jun. 5, 2012

(54) MEDICINAL COMPOSITION FOR PREVENTION OR TREATMENT OF PARASITIC PROTOZOAN INFECTION

(75) Inventors: Masataka Ihara, Tokyo (JP); Kiyosei Takasu, Kyoto (JP); Khanitha Pudhom, Bangkok (TH); Hiroshi Kitaguchi, Minamiashigara (JP); Masayuki Kawakami, Minamiashigara (JP); Kozo Sato, Minamiashigara (JP)

(73) Assignees: Fujifilm Corporation, Tokyo (JP); Masataka Ihara, Sendai-Shi (JP)

( * ) Notice: Subject to any disclaimer, the term of this patent is extended or adjusted under 35 U.S.C. 154(b) by 893 days.

(21) Appl. No.: 11/576,429

(22) PCT Filed: Sep. 30, 2005

(86) PCT No.: PCT/JP2005/018093
§ 371 (c)(1),
(2), (4) Date: Jun. 8, 2007

(87) PCT Pub. No.: WO2006/038550
PCT Pub. Date: Apr. 13, 2006

(65) Prior Publication Data
US 2010/0113789 A1    May 6, 2010

(30) Foreign Application Priority Data
Oct. 4, 2004 (JP) ................. 2004-292002

(51) Int. Cl.
*A61K 31/427* (2006.01)
*A61K 31/428* (2006.01)
*C07D 277/66* (2006.01)
*C07D 277/04* (2006.01)
*C07D 277/84* (2006.01)

(52) U.S. Cl. ......... 514/367; 514/369; 548/156; 548/186

(58) Field of Classification Search ............... None
See application file for complete search history.

(56) References Cited

U.S. PATENT DOCUMENTS

| 2,388,963 | A | * | 11/1945 | Douglas et al. | 546/175 |
| 3,806,597 | A | * | 4/1974 | Giraudon | 514/369 |
| 4,443,455 | A | * | 4/1984 | Worthington | 514/188 |
| 5,270,153 | A | * | 12/1993 | Suzuki et al. | 430/384 |
| 5,476,945 | A | * | 12/1995 | Ikegawa et al. | 548/152 |
| 5,599,825 | A | * | 2/1997 | Tatsuta et al. | 514/366 |
| 5,618,831 | A | * | 4/1997 | Shishido et al. | 514/366 |
| 5,861,424 | A |   | 1/1999 | Chen et al. |   |
| 6,506,751 | B1 | * | 1/2003 | Justus et al. | 514/236.8 |
| 6,696,473 | B2 | * | 2/2004 | Martin et al. | 514/367 |

FOREIGN PATENT DOCUMENTS

| EP | 1 623 981 A1 | 2/2006 |
| JP | 05-117148 | 5/1993 |
| JP | 06234932 A * | 8/1994 |
| JP | 2000-191531 | 7/2000 |
| JP | 2004-331545 | 11/2004 |
| WO | 96/03393 A1 | 2/1996 |
| WO | 03/007948 A1 | 1/2003 |

OTHER PUBLICATIONS

Kiyosei Takasu et al., "Rhodacyanine dyes as antimalarials. 1. Preliminary evaluation of their activity and toxicity," Journal of Medicinal Chemistry 45(5):995-998, Feb. 28, 2002.
Supplementary European Search Report cited in foreign counterpart application No. 05787692.2 (EP National Phase of the PCT/JP2005/018093 application) completed on May 19, 2010, mailed on May 31, 2010.
English Translation of the International Preliminary Report on Patentability. Written opinion of the International Searching Authority in corresponding International Application No. PCT/JP2005/018093.
Kawakami et al. "Synthesis and Evaluation of Novel Rhodacyanine Dyes That Exhibit Antitumor Activity," *J. Med. Chem.*, vol. 40, 3151-3160, 1997.
Takasu et al., "Antileishmanial Activites of Rhodacyanine Dyes," *Heterocycles*, vol. 64, 215-221, 2004.
Kawakami et al., "Structure-Activity of Novel Rhodacyanine Dyes as Antitumor Agents," *J. Med. Chem.*, vol. 41, 130-142, 1998.
Kasai, "Nettai Kansensho Chiryoyaku no Kaihatsu: Kyoekisa no Nagai Rhodacyanine no Gosei to Kassei," *Nippon Yakugakukai Nenkai Koen Yoshishu*, p. 1999, 2005.
Published International Search Report for Application No. PCT/JP2005/018093.

* cited by examiner

*Primary Examiner* — Kamal Saeed
*Assistant Examiner* — Nyeemah A Grazier
(74) *Attorney, Agent, or Firm* — Locke Lord LLP

(57) ABSTRACT

The present invention is to provide a medicinal composition for preventing or treating parasitic protozoan infections, having a high selective toxicity against parasitic protozoan infection, and a superior preventive or treating effect. A medicinal composition for preventing or treating parasitic protozoan infections comprises a compound shown by the following general formula (1) as an active ingredient

[Chemical formula 1]

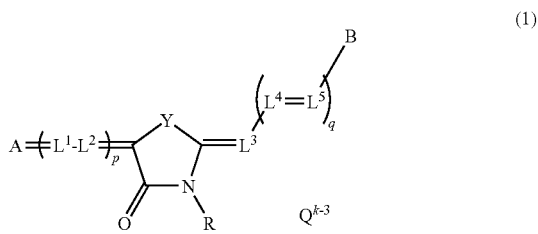

(wherein R represents an alkyl group, aryl group or heterocyclic group; A and B each independently represents a 5- or 6-membered ring containing at least one hetero atom, or a condensation ring wherein 1 or more 3- to 8-membered ring is condensed thereto; Y represents S, O, Se, or —$NR^1$— ($R^1$ represents an alkyl group, aryl group or heterocyclic group); $L^1, L^2, L^3, L^4$ and $L^5$ each independently represents a methine group; Q represents a physiologically acceptable anion; k represents an integer of 0 to 2, necessary to make the electric charge of the whole molecule 0; p and q each represents an integer of 0 to 3, wherein the sum of p and q is 1 or more, and 6 or less).

3 Claims, No Drawings

MEDICINAL COMPOSITION FOR PREVENTION OR TREATMENT OF PARASITIC PROTOZOAN INFECTION

TECHNICAL FIELD

The present invention relates to a useful medicinal composition for preventing or treating parasitic protozoan infections.

BACKGROUND ART

Even now, parasitic protozoan infections are widely known mainly around tropical or subtropical regions, and can be exemplified by malaria, leishmaniasis, African trypanosomiasis (African sleeping sickness), American trypanosomiasis (Chaga's disease), lymphatic filariasis, and babesiosis. These infections can be classified into those infecting only humans, and zoonosis also infecting domestic livestocks or small animals, both leading to significant economic and social loss. Among these diseases, there are some diseases that do not have a therapeutic agent showing a sufficient effect, or some have problems such as emergence and diffusion of drug-resistant protozoa, or side effects of therapeutic agents. Therefore, an effective agent is awaited.

For example, Pentostam, which is a therapeutic agent for leishmania contains antimony atoms in the molecule, and therefore, antimony intoxication cannot be avoided as a treatment side effect. Melarsoprol which is used in the primary treatment of African trypanosomiasis (African sleeping sickness) contains arsenic atoms in the molecule, and there is a problem that arsenic intoxication occurs as a side effect. Further, some of these diseases show severe symptoms that make it impossible to lead a normal social life, or force a patient to be bedridden necessitating care, or develop lethal symptoms. Thus, early development of a chemotherapeutic agent is indispensable.

A compound shown by general formula (1) contained in a medicinal composition of the present invention is known as an antitumor agent having a high selectivity to cancer cells (for example, see EP527,494; Japanese Laid-Open Patent Application No. 5-117148; and U85,861,424), while the use as an agent for treating or preventing parasitic protozoan infection is not known. On the other hand, the present inventors showed that a rhodacianine compound shown by the following general formula (3) has a therapeutic effect to malaria and leishmaniasis (for example, see Japanese Laid-Open Patent Application No. 2000-191531; Japanese Laid-Open Patent Application No. 2003-034640; Japanese Laid-Open Patent Application No. 2003-034641; and Japanese Laid-Open Patent Application No. 2003-034642). However, the correlation between parasitic infection and effect of an agent has not been much clarified, and under such present circumstance, it is quite difficult to find out a structure of a compound effective to protozoan infections. In other words, it was not clear whether a compound shown by general formula 1 of the present invention has an effect on protozoan infection or not, and such effect was not predictable.

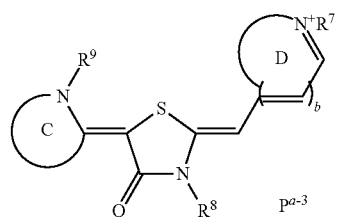

(wherein $R^7$ and $R^9$ each independently represent an alkyl group; $R^8$ represents an alkyl group, aryl group or heterocyclic group; C and D each independently represents an atom group necessary for forming a 5- or 6-membered heterocycle; P represents a physiologically acceptable anion; a represents an integer of 0 to 2, necessary to make the electric charge of the whole molecule 0; b represents 0 or 1.)

Patent document 1: EP 527,494
Patent document 2: Japanese Laid-Open Patent Application No. 5-117148
Patent document 3: U.S. Pat. No. 5,861,424
Patent document 4: Japanese Laid-Open Patent Application No. 2000-191531
Patent document 5: Japanese Laid-Open Patent Application No. 2003-034640
Patent document 6: Japanese Laid-Open Patent Application No. 2003-034641
Patent document 7: Japanese Laid-Open Patent Application No. 2003-034642

DISCLOSURE OF THE INVENTION

Object to be Solved by the Invention

The object of the invention is to provide a medicinal composition for preventing or treating parasitic protozoan infection having a high selective toxicity and having a superior treatment or preventing effect against parasitic protozoan infection.

Means to Solve the Object

In order to solve the above object, the present inventors assayed growth effects of protozoa causing diseases on various compounds, and further conducted keen studies by estimating cellular toxicity against mammal cells, which is an index of side effect. Thus, they found out that a compound shown by general formula (1) of the present invention is very effective to parasitic protozoan infections, and completed the present invention.

In other words, the present invention relates to ("1") a medicinal composition for preventing or treating parasitic protozoan infections comprising a compound shown by the following general formula (1) as an active ingredient;

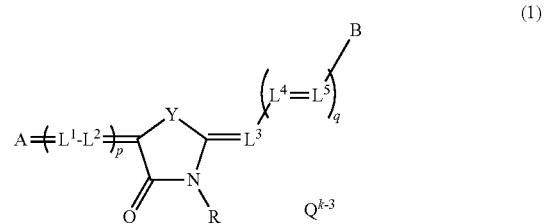

(wherein R represents an alkyl group, aryl group or heterocyclic group; A and B each independently represents a 5- or 6-membered ring containing at least one hetero atom, or a condensation ring wherein 1 or more 3- to 8-membered ring is condensed thereto; Y represents S, O, Se, or —NR$^1$— (R$^1$ represents an alkyl group, aryl group or heterocyclic group); L$^1$, L$^2$, L$^3$, L$^4$ and L$^5$ each independently represents a methine group; Q represents a physiologically acceptable anion; k represents an integer of 0 to 2, necessary to make the electric charge of the whole molecule 0; p and q each represents an integer of 0 to 3, wherein the sum of p and q is 1 or more, and 6 or less.); ("2") the medicinal composition for preventing or treating parasitic protozoan infections according to "1", wherein L$^1$ and/or L$^5$ is a substituted methine group, and atoms constituting L$^1$ and A and/or atoms constituting L$^5$ and B are bound to form a 5- or 6-membered ring; ("3") the medicinal composition for preventing or treating parasitic protozoan infections according to "1" or "2", wherein a compound shown by general formula (1) is a compound shown by the following general formula (2);

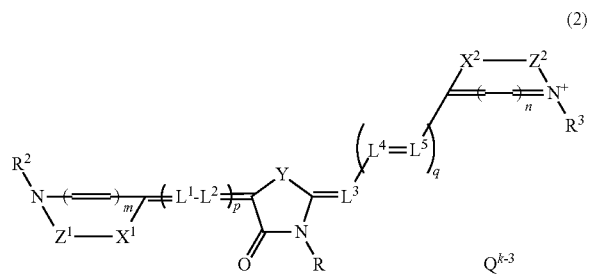

(wherein R$^2$ and R$^3$ each independently represents an alkyl group; X$^1$ and X$^2$ each independently represents S, O, Se, —CH=CH—, —CR$^4$R$^5$— (R$^4$ and R$^5$ each independently represents an alkyl group), or —NR$^6$— (R$^6$ represents an alkyl group, aryl group, or heterocyclic group); Z$^1$ and Z$^2$ each independently represents a 5- or 6-membered ring, or a condensation ring wherein 1 or more 3- to 8-membered ring is condensed thereto; m and n each represents 0 or 1).

Moreover, the present invention relates to: ("4") the medicinal composition for preventing or treating parasitic protozoan infections according to "3", wherein L$^1$ and/or L$^5$ is a substituted methine group, L$^1$ and L$^2$ and/or L$^5$ and R$^3$ are bound to form a 5- or 6-membered ring; ("5") the medicinal composition for preventing or treating parasitic protozoan infections according to any one of "1" to "4", wherein Q is halogen ion, sulfonate ion, or carboxylate ion; ("6") the medicinal composition for preventing or treating parasitic protozoan infections according to any one of "1" to "5", wherein the parasitic protozoan infection is malaria, leishmaniasis, African trypanosomiasis, or American trypanosomiasis.

BEST MODE OF CARRYING OUT THE INVENTION

A medicinal composition for treating or preventing parasitic protozoan infections of the present invention (hereinafter referred to as "medicinal composition of the present invention") is not particularly limited as long as it is a medicinal composition comprising a compound shown by the following general formula (1) as an active ingredient, and it can contain one or more kind(s) of compound shown by general formula (1) as an active ingredient, and the compound is usually contained together with a pharmaceutically acceptable carrier or diluent.

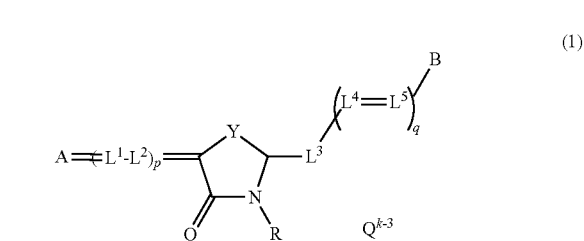

In general formula (1), R represents an alkyl group, aryl group or heterocyclic group. As an alkyl group shown by R in general formula (1), one with 1 to 15 carbons is preferred, and one with 1 to 7 carbons is more preferred, and it can be linear, branched, or cyclic. The alkyl group may be substituted, and preferred substituents include: an alkyl group with 1 to 15 carbons, alkenyl group with 2 to 15 carbons, alkynyl group with 2 to 15 carbons, alkoxy group with 1 to 15 carbons, aryloxy group with 6 to 15 carbons, halogen atom (chlorine, bromine, fluorine, iodine, etc.), aryl group with 6 to 15 carbons, hydroxyl group, amino group, amino group substituted by alkyl group or aryl group, acylamino group, sulfonylamino group, carbamoyl group, sulfamoyl group, carboxyl group, alkoxycarbonyl group with 2 to 15 carbons, acyloxy group with 2 to 15 carbons, 5- or 6-membered heterocycle (pyrrole ring, furan ring, piperidine ring, morpholine ring, pyridine ring, etc.), cyano group, and nitro group. These groups may be further substituted each other. Specific examples of alkyl group represented by R include methyl group, ethyl group, hydroxyethyl group, 2-propenyl group, benzyl group, propyl group, and butyl group.

As an aryl group represented by R of general formula (1), one with 5 to 15 carbons is preferred, and one with to 10 is more preferred. The aryl group may be substituted, and as substituents, similar ones as for the above alkyl group can be exemplified. Specific examples of aryl group represented by R include phenyl group, tolyl group, p-chlorophenyl group, 1-naphthyl group, and 2-naphtyl group.

A heterocyclic ring represented by R in general formula (1) may be a saturated ring or unsaturated ring, a 5- to 8-membered ring is preferred, and a 5- or 6-membered ring is more preferred. As hetero atoms, nitrogen atom, oxygen atom, sulfur atom, selenium atom, tellurium atom, and phosphorus atom can be exemplified, and nitrogen atom, oxygen atom, sulfur atom, and selenium atom are preferred. The heterocyclic group may be substituted, and as substituents, similar ones as for the above alkyl group can be exemplified. Specific examples of heterocyclic ring represented by R include pyrrole group, furan group, piperidine group, morpholine group, piperazine group, pyridine group, and pyrrolidine group.

In general formula (1), A and B each independently represents a 5- or 6-membered ring including at least 1 hetero atom, or a condensation ring wherein 1 or more 3- to 8-membered ring is condensed thereto. A 5- or 6-membered ring including at least 1 hetero atom represented by A and B in general formula (1) may be a saturated ring or unsaturated ring. Examples of hetero atoms included in the 5- or 6-membered ring include nitrogen atom, oxygen atom, sulfur atom, selenium atom, tellurium atom, silicon atom, phosphorus atom, and it is preferred that at least 1 nitrogen atom is included. Further, a 3- to 8-membered ring of a condensation ring wherein 1 or more 3- to 8-membered ring is condensed to the above 5- or 6-membered ring, which is represented by A and B, may be a saturated ring or unsaturated ring, and can be exemplified by a cyclopropane ring, cyclopropene ring, cyclobutane ring, cyclobutene ring, cyclopentane ring, cyclopentene ring, cyclohexane ring, cyclohexene ring, cycloheptane ring, cycloheptene ring, cyclooctane ring, cyclooctene ring, benzene ring, naphthalene ring, anthracene ring, phenanthrene ring, thiophene ring, pyridine ring. Among these, 5- or 6-membered ring is particularly preferred. Moreover, A and B may have 1 or more substituents, and as substituents, similar ones as for the alkyl group represented by R in general formula (1) can be exemplified.

In general formula (1), Y represents S, O, Se or —$NR^1$—, and among these, S or O is preferred. Meanwhile, $R^1$ represents an alkyl group, aryl group or heterocyclic group, which has the same meaning as the alkyl group, aryl group or heterocyclic group represented by R in general formula (1), respectively.

In general formula (1), $L^1$, $L^2$, $L^3$, $L^4$ and $L^5$ each independently represents a methine group, and may have a substituent. As substituents, alkyl group with 1 to 15 carbons (for example, methyl, ethyl, propyl, butyl groups, etc.), aryl group with 6 to 15 carbons (for example, phenyl, tolyl, naphthyl groups, etc.), halogen atom (chlorine, bromine, fluorine and iodine), alkenyl group with 2 to 15 carbons (for example, ethenyl group, 1-propenyl group, etc.), alkenyl group with 2 to 15 carbons (for example ethinyl group, etc.), alkoxy group with 1 to 15 carbons (for example, methoxy, ethoxy groups, etc.) can be exemplified. Further, when $L^1$ is a substituted methine group, atoms constituting $L^1$ and A may be bound to form a 5- or 6-membered ring. Similarly, when $L^5$ is a substituted methine group, atoms constituting $L^5$ and B may be bound to form a 5- or 6-membered ring. As such 5- or 6-membered ring, a 5-membered heteroring (for example, pyrroline ring) and 6-membered heteroring (for example, tetrahydropyrrolidine group, oxazine group, etc.) can be exemplified.

In general formula (1), Q represents a physiologically acceptable anion. Such physiologically acceptable anion relates to an ion that is nontoxic when a compound shown by general formula (1) is administered to a recipient, and that dissolves the compound shown by general formula (1) to an aqueous system. Examples of physiologically acceptable anion represented by Q include: halogen ions such as chlorine ion, bromine ion, iodine ion; sulfonate ion such as aliphatic and aromatic sulfonate ions including methanesulfonate ion, trifluoromethanesulfonate ion, p-toluenesulfonate ion, naphthalenesulfonate ion, 2-hydroxyethanesulfonate ion; sulfamate ion such as cyclohexanesulfamate ion; sulfate ion such as methylsulfate ion and ethylsulfate ion; hydrogen sulfate ion; borate ion; alkyl and dialkyl phosphate ions such as diethylphosphate ion and methyl hydrogen phosphate ion; pyrophosphate ion such as trimethylpyrophosphate ion; carbonate ion (carbonate ion wherein carboxy group and hydroxyl group are substituted is suitably used); carbonate ion; hydrogencarbonate ion and hydroxide ion; acetate ion; propionate ion; valerate ion; citrate ion; maleate ion; fumarate ion; lactate ion; succinate ion; tartrate ion; benzoate ion. Halogen ion, sulfonate ion or carboxylate ion is preferred.

In general formula (1), k represents an integer of 0 to 2 necessary to make the electric charge of the whole molecule 0; p and q each represents an integer of 0 to 3, wherein the sum of p and q is 1 or more, and 6 or less.

Moreover, as a compound shown by the above general formula (1), a compound shown by the following formula (2) is preferred.

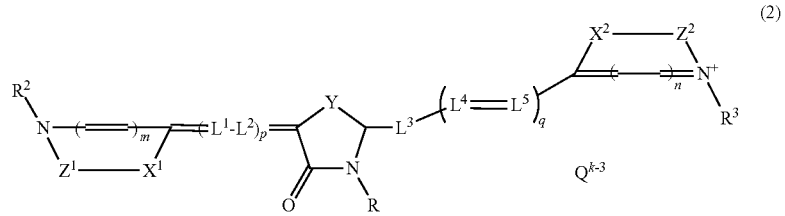

In general formula (2), $R^2$ and $R^3$ each independently represents an alkyl group, which has the same meaning as the alkyl group represented by R in general formula (1). Moreover, when $L^1$ is a substituted methine group, $L^1$ and $R^2$ may be bound to form a 5- or 6-membered ring, and when $L^5$ is a substituted methine group, $L^5$ and $R^3$ may be bound to form a 5- or 6-membered ring. As a ring formed when $L^1$ and $R^2$, or $L^5$ and $R^3$ are bound, a 5-membered heteroring (for example, pyrroline ring, etc.) and 6-membered heteroring (for example, tetrahydropyrrolidine group, oxazine group, etc.) can be exemplified.

In general formula (2), $X^1$ and $X^2$ each independently represents S, O, Se, —CH=CH—, —$CR^4R^5$—, or —$NR^6$—; $R^4$ and $R^5$ each independently represents an alkyl group; and $R^6$ represents an alkyl group, aryl group or heterocyclic group. An alkyl group represented by $R^4$ to $R^6$ and an aryl group and heterocyclic group represented by $R^6$ are the same as those represented by R in general formula (1).

In general formula (2), $Z^1$ and $Z^2$ each independently represents an atom group necessary to form a 5- or 6-membered ring, or a condensation ring wherein 1 or more 3- to 8-membered ring is condensed thereto. A 5- or 6-membered ring formed by an atom group represented by $Z^1$ and $Z^2$ relates to a ring formed on each ring section including N, $X^1$, $Z^1$ or $N^+$, $X^2$, $Z^2$ of a compound shown by general formula (2). Specific examples of $Z^1$ and $Z^2$ include methylene group, ethylene group, and vinylene group.

Specific examples of heterocycle which is a 5- or 6-membered ring formed by an atom group represented by $Z^1$ and $Z^2$ include: thiazole ring (for example, thiazole, 4-methylthiazole, 4-phenylthiazole, 4,5-diphenylthiazole, 4,5-dimethylthiazole, etc.), benzothiazole ring (for example, benzothiazole, 5-methylbenzothiazole, 5-phenylbenzothiazole, 5-metoxybenzothiazole, 4-fluorobenzothiazole, 5, 6-dioxymethylenebenzothiazole, 5-nitrobenzothiazole, 5-trifluoromethylbenzothiazole, 5-metoxycarbonylbenzothiazole, 6-hydroxybenzothiazole 5-cyanobenzothiazole, 5-iodobenzothiazole, etc.), naphtothizaole ring (for example, α-naphtothiazole, β-naphtothiazole, γ-naphtothiazole, 5-methoxy-β-naphtothiazole, 8-methoxy-α-naphtothiazole, 6-methoxy-8-acetoxy-β-naphtothiazole, 8,9-dihydroxy-β-nathtothiazole, etc.), oxazole ring (for example, 4-methyloxazole, 4-phenyloxazole, 4,5-diphenyloxazole, 4-phenoxyoxazole, etc.) benzoxazole ring (for example, benzoxazole, 5-chlorobenzoxazole, 5,6-dimethylbenzoxazole, 6-hydroxybenzoxazole, 5-phenylbenzoxazole, etc.), naphtoxazole ring (for example, α-naphtoxazole, β-naphtoxazole, γ-naphtoxazole, etc.), selenazole ring (for example, 4-methylselenazole, 4-phenylselenazole, etc.), benzselenazole ring (for example, benzselenazole, 5-chlorobenzselenazole, 5,6-dimethylbenzselenazole, 6-hydroxybenzselenazole, 5-phenylbenzselenazole, etc.), thiazoline ring (for example, thiazoline, 4,4-dimethylthiazoline, etc.), 2-pyridine ring (for example, 2-pyridine, 5-methyl-2-pyridine, 5-methoxy-2-pyridine, 4-chloro-2-pyridine, 5-carbamoyl-2-pyridine, 5-methoxycarbonyl-2-pyridine, 4-acetylamino-2-pyridine, 6-methylthio-2-pyridine, 6-methyl-2-pyridine, etc.), 4-pyridine ring (for example, 4-pyridine, 3-methoxy-4-pyridine, 3,5-dimethyl-4-pyridine, 3-chloro-4-pyridine, 3-methyl-4-pyridine, etc.), 2-quinoline ring (for example, 2-quinoline, 6-methyl-3-quinoline, 6-chloro-2-quinoline, 6-ethoxy-2-quinoline, 6-hydroxy-2-quinoline, 6-nitro-2-quinoline, 6-acetylamino-2-quinoline, 8-fluoro-2-quinoline, etc.), 4-quinoline ring (for example, 4-quinoline, 6-methoxy-4-quinoline, 6-acetylamino-4-quinoline, 8-chloro-4-quinoline, 8-trifluoromethyl-4-quinoline, etc.), 1-isoquinoline ring (for example, 1-isoquinoline, 6-methoxy-1-isoquinoline, 6-acetylamino-1-isoquinoline, 6-chloro-1-isoquinoline, etc.), 3,3-dialkylindolenine ring (for example, 3,3-dimethylindolenine, 3,3,7-trimethylindolenine, 5-chloro-3,3-dimethylindolenine, 5-ethoxycarbonyl-3,3-dimethylindolenine, 5-nitro-3,3-dimethylindolenine, 3,3-dimethyl4,5-phenyleneindolenine, 3,3-dimethyl-6,7-phenyleneindolenine, 5-acetylamino-3,3-diethylindolenine, 5-diethylamino-3,3-dipropylindolenine, 5-benzoylamino-3-ethyl-3-methylindolenine, etc.), imidazole ring (for example, imidazole, 1-methyl-4-phenylimidazole, 1-benzyl-4,5-dimethylimidazole, etc.), benzimidazole ring (for example, benzimidazole, 1-methylbenzimidazole, 1-methyl-5-trifluoromethylbenzimidazole, 1-ethyl-5-chlorobenzimidazole, 1-phenyl-5-methoxycarbonylbenzimidazole, 1-ethyl-5-dimethylaminobenzimidazole, etc.), naphtoimidazole ring (for example, 1-methyl-α-naphtoimidazole, 1-methyl-5-methoxy-β-naphtoimidazole, etc.).

Further, $Z^1$ and $Z^2$ may be a condensation ring, wherein or more 3- to 8-membered ring, preferably 5- or 6-membered ring is condensed to the above 5- or 6-membered ring. Such 1 or more 3- to 8-membered ring may be a saturated ring or unsaturated ring, and can be exemplified by cyclopropane ring, cyclopropene ring, cyclobutane ring, cyclobutene ring, cyclopentane ring, cyclopentene ring, cyclohexane ring, cyclohexene ring, cycloheptane ring, cycloheptene ring, cyclooctane ring, cyclooctene ring, benzene ring, naphthalene ring, anthracene ring, phenanthrene ring, thiophene ring, and pyridine ring. Further, the above 5- or 6-membered ring and condensation ring may have 1 or more substituents, and as substituents, similar ones as for the alkyl group represented by R in general formula (1) can be exemplified.

In general formula (2), m and n each represents 0 or 1.

Compounds represented by general formula (1) and general formula (2) of the present invention may be easily manufactured from known starting materials according to known methods described in EP 527,494, Japanese Laid-Open Patent Application No. 5-117148, US Patent Application No. 692,347, a non-patent document by E. B. K. Nott et al (J. Chem. Soc. Page 4762 (1952), p. 949 (1955)), and a non-patent document by Kawakami et al. (J. Med. Chem., page 3151 (1997)). All of these disclosures are understood to be described in the present specification.

Typical examples of compounds shown by general formulae (1) and (2) of the present invention include the following, while it is not limited to these compounds.

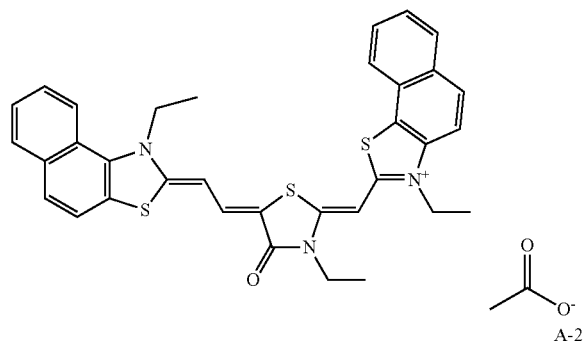

A-1

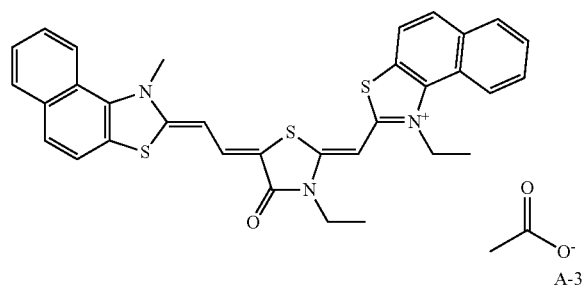

A-2

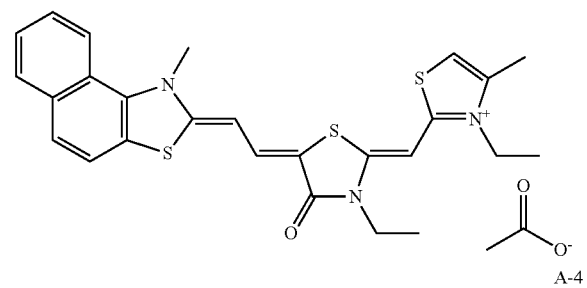

A-3

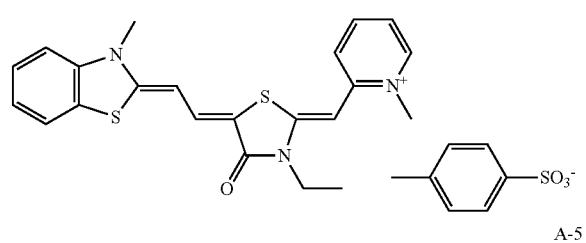

A-4

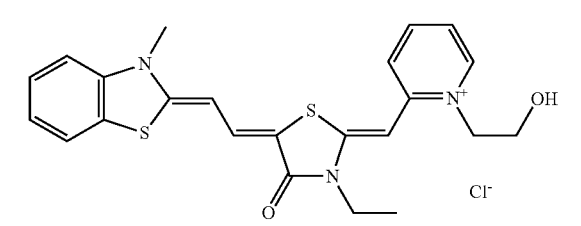

A-5

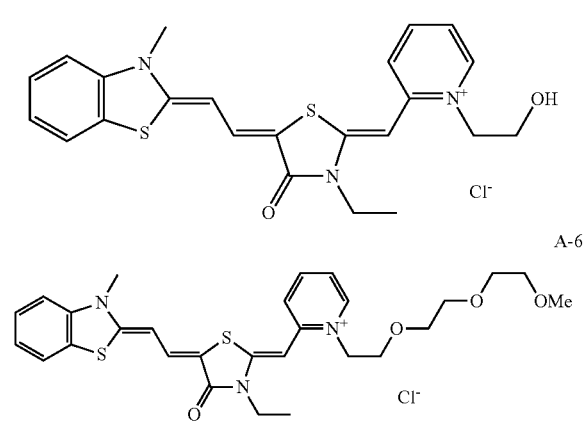

A-6

A-7
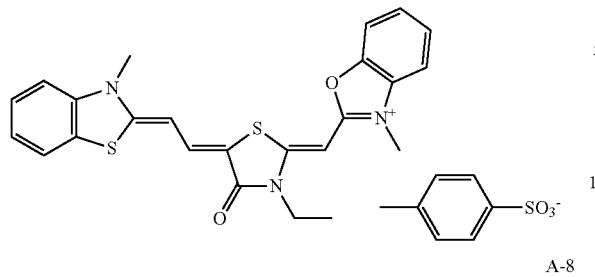
A-8
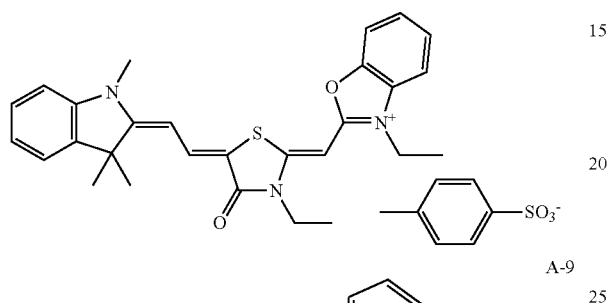
A-9
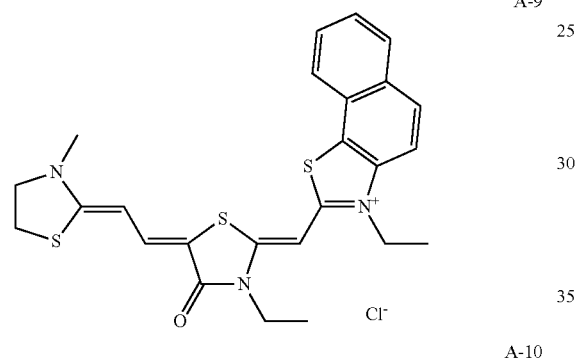
A-10
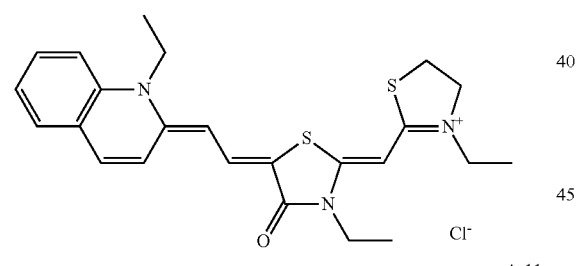
A-11
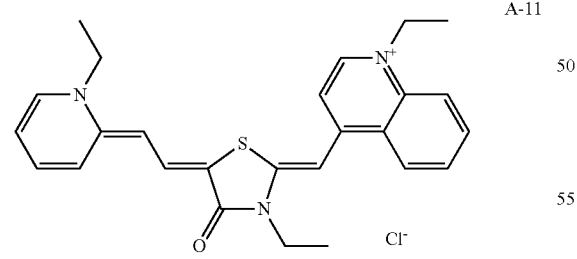
A-12
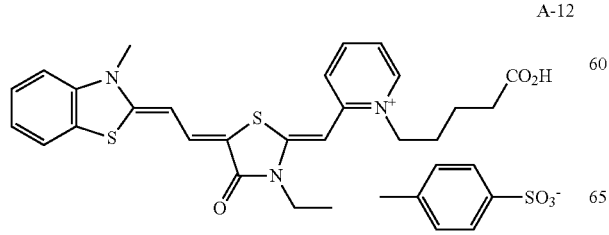
A-13
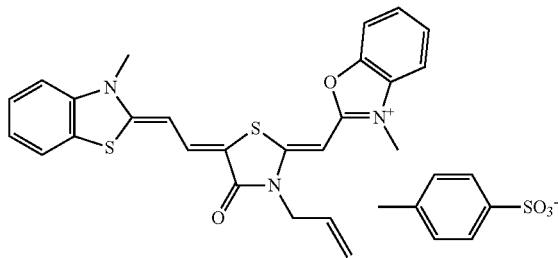
A-14
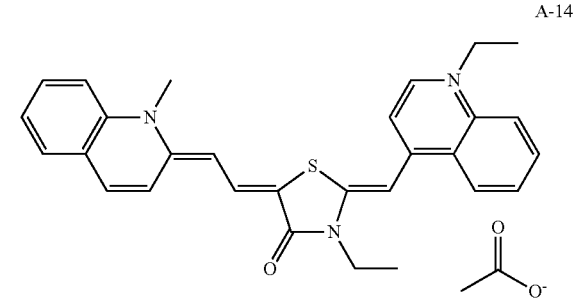
A-15
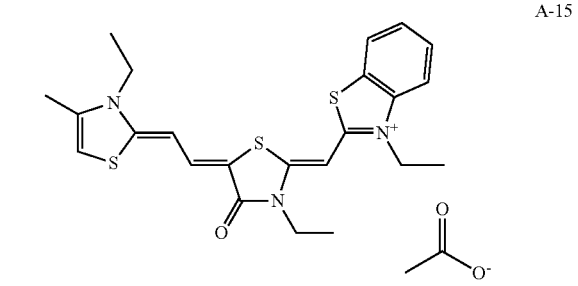
A-16
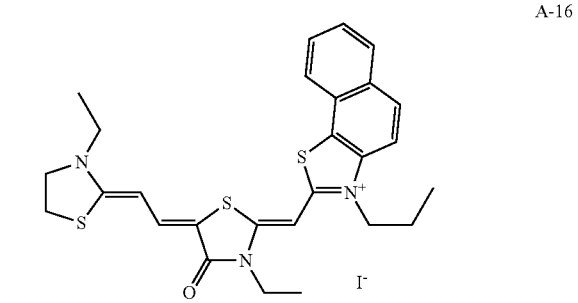
A-17
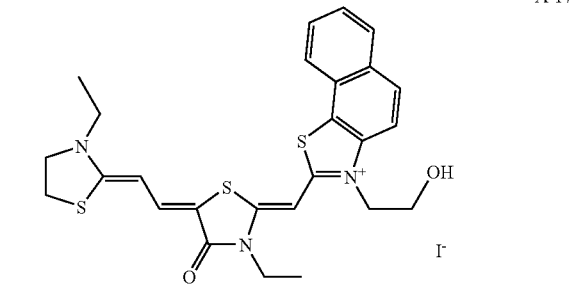

-continued

A-18

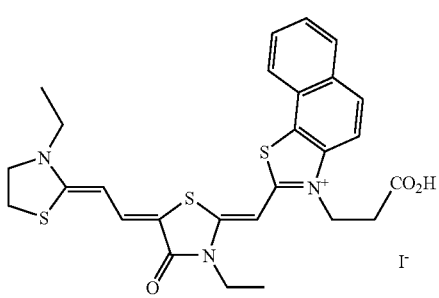

The medicinal composition of the present invention may be used effectively for preventing or treating various types of diseases caused by parasitic protozoan infections, including malaria, leishmaniasis, African trypanosomiasis (African sleeping sickness), American trypanosomiasis (Chaga's disease), lymphatic filariasis, and babesiosis. The medicinal composition of the present invention may contain anti-protozoan infective agents which are used conventionally, according to need. Suitable examples of anti-protozoan infection agents which are used conventionally include: chloroquine, mefloquine, artemisinin, atavaquone, pyrimethamine (treating agents for malaria infection); suramin, pentamidine (treating agents for African trypanosomiasis); benznidazole, primaquine (treating agents for American trypanosomiasis); pentostam, Amphotericin B, miltefosine (treating agents for leishmaniasis).

Moreover, as medicinal carriers or diluents that can be used with the compounds shown by general formulae (1) and (2) of the present invention, medicinal carriers or diluents that are commonly used conventionally may be used, and examples include the following: glucose; saccharose; lactose; ethyl alcohol; glycerol; mannitol; sorbitol; pentaerythritol; diethylene glycol; propylene glycol, dipropylene glycol, polyethylene glycol 400, other polyethylene glycol; mono-, di- and tri-glyceride of fatty acids including trilaurate glyceryl and distearate glyceryl; pectin; starch; arginine acid; xylose; talc; lycopodium; olive oil; oil and fat including peanut oil, castor oil, corn oil, safflower oil, wheat germ oil, sesame oil, cotton seed oil, sunflower oil and oleum morrhuae; gelatin; lecithin; silica; cellulose; cellulose derivatives including methylhydroxypropyl cellulose, methyl cellulose and hydroxyethyl cellulose; salts of fatty acids with 12 to 22 carbon atoms including calcium stearate, calcium laurate, magnesium oleate, calcium palminate, calcium behenate and magnesium stearate; cyclodextrins (for example, α-cyclodextrin, β-cyclodextrin, γ-cyclodextrin, hydroxyethyl-β-cyclodextrin, hydroxypropyl-β-cyclodextrin, dihydroxypropyl-β-cyclodextrin, carboxymethylethyl-β-cyclodextrin, cycloawaodorin, and dimethyl-β-cyclodextrin, etc.); emulsifier (for example, ester of saturated and unsaturated fatty acids with 2 to 22, particularly 10 to 18 carbon atoms, with monovalent aliphatic alcohol or polyvalent alcohol with 1 to 20 carbon atoms including glycol, glycerine, diethylene glycol, pentaerythritol, ethyl alcohol and butyl alcohol, octadecyl alcohol); and silicone such as dimethylpolysiloxane.

Further, pharmaceutically effective dose and administration method or administration means of the compound shown by general formulae (1) and (2) of the present invention depend on types of parasitic protozoa being the cause of the infection, habitats of protozoa, seriousness of diseases, treatment strategies, age, body weight, sex, and general health conditions of the patient, and (genetic) racial background of the patient. However, generally, the dosage of the present invention is 1 to 2000 mg, more generally 50 to 500 mg/day/70 kg of body weight. Suitable administration method include, for example, injecting intravenously, intraperitoneally, or subcutaneously as diluted to 5% glucose aqueous solution, or in a form accompanied with the above carrier or diluent; administrating orally; or applying to skin.

In order to clarify the effectivity of the compound shown by general formulae (1) and (2) of the present invention and its medicinal composition, Examples will be shown in the following, while the technical scope of the present invention will not be limited to these exemplifications.

Example 1

1-1 Culture of Drug Sensitive-*Plasmodium falciparum*

In the present example, protozoa of *Plasmodium falciparum* FCR-3 strain was used. RPMI-1640 medium sterilized with a filter was used in the experiment. pH was adjusted to 7.4, and human serum was added to be 10%. Malarial parasites were cultured under 5% $O_2$ concentration, 5% $CO_2$ concentration, 90% $N_2$ concentration, and at a temperature of 36.5° C.

1-2 Drug Sensitive-*Plasmodium falciparum* Growth Inhibition Screening Test

Cultured malarial parasite infected-erythrocytes were collected by centrifugation, and washed in a medium containing serum. Non-infected erythrocytes were added so that the primary infection rate is 0.3%. Hematocrit level at that time was 3%. The compounds of the present invention to be used in the test and the positive target drugs (chloroquine, quinine) were dissolved in dimethylsulfoxide (DMSO) to make a test solution of a predetermined concentration. The test solution was added in an amount of 5 to 10 µl in a 24-well culture plate. To the control, DMSO was added in an amount of 10 µL/well. Test solutions were taken by duplicates. Subsequently, *Plasmodium falciparum* culture solution previously prepared to a predetermined concentration was added, pipetted quietly, and suspended in the medium similarly. Culture plate was cultured for 72 hours in a $CO_2$—$O_2$—$N_2$(5%, 5%, 90%) incubator. Thin layer smear preparations were prepared for each well, and after performing Diff-Quick staining, the preparations were measured with a microscope (oil immersion, 1,000×), and malarial parasite infection rates of the test solution added-group and of the control group were calculated. Growth inhibition rate was calculated with the following formula from the malarial parasite infection rate obtained in the above, to obtain a 50% growth inhibition concentration ($EC_{50}$).

Growth inhibition rate (%)={1−(b−a)/(c−a)}×100 a: early infection rate
b: infection rate when test solution was added
c: infection rate of the control 1-3 Growth Inhibition Test of Mouse FM3A Cells F28-7 strain which is a wild-type of the mouse breast cancer derived FM3A cell was used. As for a medium, immobilized fetal bovine serum was added to a ES medium at 2%, which medium was cultured under $CO_2$ concentration 5%, at 37° C. Doubling time of FM3A cells under that condition was approximately 12 hours. Pre-culture was conducted and cells which have entered the logarithmic growth phase were diluted in a medium to be 5×10⁴ cells/mL Those prepared when measuring malarial activity were used as a sample. Sample solution was added in an amount of to 10 µL in a 24-well culture plate (the final concentration was $1\times10^{-4}$ to $1\times10^{-5}$, by adding media etc). Compounds were taken by duplicates, and wells added with 10 µL DMSO were prepared at the same time as a control. Next, cultured cell suspension previously prepared was added in an amount of 990 to 995 μL, pipetted quietly and suspended in a medium similarly. After culturing 48 hours, the cells were counted with a cell controller (CC-108, Toa. Medical Electrics) for each well. Growth rate was calculated with the following formula, to obtain a 50% growth inhibition rate ($EC_{50}$).

Growth rate (%)={$(C-A)/(B-A)$}×100

A: primary cell count
B: cell count of the control, 2 days after
C: cell count of wells added with a sample, 2 days after Cell growth inhibiting activity was calculated from cell count of wells added with a sample, and cell count of the control. From this result, cell toxicity of a sample was estimated.

1-4 Determination of Drug Efficacy Against Drug-Sensitive *Plasmodium*

Anti-malarial activity of a sample was estimated from EC50 values of the sample against drug sensitive-*Plasmodium falciparum* and mouse FM3A cells. Chemotherapy index used as an index of selective toxicity against drug sensitive-*Plasmodium falciparum* was calculated with the following formula, to determine drug efficacy.

Chemotherapy index=($EC_{50}$ value of a sample against mouse FM3A cells)/($EC_{50}$ value of a sample against drug sensitive-*Plasmodium falciparum*)

$EC_{50}$ values of samples of the compounds of the present invention and the positive target drugs against drug sensitive-*Plasmodium falciparum* and mouse FM3A cells are shown in Table 1.

TABLE 1

| compounds | 50% growth inhibition concentration (μM) | | Selective toxicity |
|---|---|---|---|
| | P. falciparum FCR | Cytotoxicity FM3A | |
| A-2 | 0.10 | 0.80 | 8 |
| A-3 | 0.075 | 1.5 | 20 |
| A-11 | 0.60 | >14 | >23 |
| quinine | 0.11 | 100 | 910 |
| chloroquine | 0.018 | 32 | 1780 |

The compounds of the present invention showed a similar or superior growth inhibition effect compared to existing drugs, quinine and chloroquine. Moreover, they did not show potent toxicity against normal cells.

Example 2

2-1 Culture of Chloroquine Resistant-*Plasmodium falciparum*

In the present example, protozoa of *Plasmodium falciparum* K1 strain was used. RPMI-1640 medium sterilized with a filter to which human serum was added to be 5%, was used in the experiment. Malarial parasites were cultured under 3% $O_2$ concentration, 4% $Co_2$ concentration, 93% $N_2$ concentration, and at a temperature of 37° C.

2-2. Chloroquine Resistant-*Plasmodium falciparum* Growth Inhibition Screening Test The compounds of the present invention to be used in the present test and the positive target drug (chloroquine) were dissolved in DMSO to make a test solution of a predetermined concentration. Cultured malarial parasite infected-erythrocytes were collected by centrifugation, and diluted with non-infected erythrocyte so that the early infection rate is 0.15%. Hematocrit level at that time was 2.5%. 200 μL of malaria infected solution was added to wells of a 96-well culture plate, and adjusted by adding a test solution containing drug of a predetermined concentration or a drug-free DMSO. Test solutions were taken by duplicates. After culturing for 48 hours at 37° C., 0.5 μCi radioactive tritium (3H)-labeled hypoxanthine was added to each well. After further culturing for 24 hours under the same conditions, it was collected on a glass fiber filter and washed with distilled water. Radiation intensity was measured with a beta plate liquid scintillation counter (Wallac), and malarial parasite infection rates of the test solution added group and of the control group were calculated. Growth inhibition rate was calculated with the following formula based on the malarial parasite infection rate obtained in the above, to obtain a 50% growth inhibition concentration ($EC_{50}$).

Growth inhibition rate (%)={$1-(b-a)/(c-a)$}×100 a: early infection rate
b: infection rate when test solution was added
c: infection rate of the control 2-3. Growth Inhibition Test of Rat L6 Cells Rat derived-L6 cells (rat skeletal myoblast cell) were used. As medium, RPMI1640 medium was supplemented so that L-glutamin (200 mM) is 1%, and fetal bovine serum 10%, and the medium was cultured under $CO_2$ concentration 5%, at 37° C. The compounds of the present invention and the target drugs to be used in the test were dissolved in DMSO, to make a test solution of a predetermined concentration. Pre-culture was conducted and medium containing cells which have entered the logarithmic growth phase was taken to wells of a 96-well culture plate. Then, a test solution containing drug of a predetermined concentration or a drug-free DMSO was added. Test solutions were taken by duplicates. Culture plate was cultured for 72 hours in an incubator, to test the growth inhibition activity. Test was conducted as follows.

10 μl of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, and residual rate of L6 cells of the test solution added group, and that of the control was calculated. Based on the cell residual rate obtained in the above, growth inhibition rate to L6 cells was calculated, to obtain a 50% growth inhibition concentration (EC50).

Growth inhibition rate (%)={$(C-A)/(B-A)$}×100

A: primary cell count
B: cell count of control, 3 days after
C: cell count of wells added with a sample, 3 days after 2-4. Determination of Drug Efficacy Against Chloroquine Resistant-Plasmodium Anti malarial activity of a sample was estimated from $EC_{50}$ values of the sample against chloroquine resistant-*Plasmodium falciparum* and rat L6 cells. Chemotherapy index used as an index of selective toxicity against chloroquine resistant-*Plasmodium falciparum* was calculated with the following formula, to determine drug efficacy.

Chemotherapy index=($EC_{50}$ value of a sample against rat L6 cells)/($EC_{50}$ value of a sample against chloroquine resistant-*Plasmodium falciparum*)

$EC_{50}$ values of samples of the compounds of the present invention and the positive target drug against chloroquine resistant-*Plasmodium falciparum* and rat L6 cells, as well as selective toxicity index are shown in Table 2.

TABLE 2

| compounds | 50% growth inhibition concentration (μM) | | Selective toxicity |
|---|---|---|---|
| | P. falciparum K1 | Cytotoxicity L6 | |
| A-1 | 0.011 | 30 | 2700 |
| A-4 | 0.12 | 76 | 660 |
| A-5 | 0.27 | 42 | 150 |
| A-6 | 0.19 | 44 | 236 |
| A-8 | 0.014 | 1.8 | 130 |
| A-9 | 0.074 | 8.1 | 110 |
| A-10 | 0.12 | 20 | 170 |
| A-12 | 0.21 | 17 | 84 |
| A-14 | 0.14 | 9.1 | 67 |
| A-15 | 0.076 | 22 | 291 |
| A-17 | 0.038 | 53 | 1400 |
| chloroquine | 0.15 | — | — |

The compounds of the present invention showed a similar or superior growth inhibition effect compared to the existing drug, chloroquine. Moreover, they did not show potent toxicity against normal cells. In other words, it can be estimated that it is effective as an anti-drug resistant malarial drug.

Example 3

3-1. Culture of African Trypanosoma Protozoa

In the present example, protozoa of *Trypanosoma brucei* rhodensiense (STIB 900 strain), a trypamastigote living in blood stream, was used. The medium used in the experiment was a MEM medium which was sterilized with a filter and supplemented with 25 mM N-2-hydroxyethylpiperazine-2-ethansulfonic acid CREPES), 1 g/L glucose, 1% MEM non-essential amino acid, 0.2 mM 2-mercaptoethanol, 2 mM sodium pyruvate, 0.1 mM hypoxanthine, and 15% heat-treated horse serum. The protozoa was cultured in an atmosphere of $CO_2$ concentration 5%, at a temperature of 37° C.

3-2. African Trypanosome Protozoa Growth Inhibition Screening Test

The compounds of the present invention to be used in the present test and the positive target drug (melarsoprol) were dissolved in DMSO to make a test solution of a predetermined concentration. A medium containing $8×10^3$ protozoa, and a test solution containing a drug of a predetermined concentration or a drug-free DMSO were added to wells of a 96-well culture plate, and subsequently, medium was added so that the amount in each well becomes 100 μL. Test solutions were taken by duplicates. After culturing the culture plate for 72 hours in an incubator, growth inhibition activity was tested. Test was conducted as follows. 10 μL of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, to calculate the trypanosome protozoa infected rate of the test solution added-group, and of the control group. From the protozoan infection rate obtained in the above, growth inhibition rate was calculated with the following formula, to obtain a 50% growth inhibition concentration ($EC_{50}$).

Growth inhibition rate (%)={1−(b−a)/(c−a)}×100 a: early infection rate
b: infection rate when test solution was added
c: infection rate of the control 3-3. Determination of Drug Efficacy of African Trypanosome Chemotherapy index used as an index of selective toxicity against African trypanosome protozoa was calculated with the following formula, to determine drug efficacy.

Chemotherapy index=($EC_{50}$ value of a sample against rat L6 cells)/($EC_{50}$ value of a sample against African trypanosome protozoa)

$EC_{50}$ values of samples of the compounds of the present invention and the positive target drug against African trypanosome protozoa and rat L6 cells, as well as selective toxicity index are shown in Table 3.

TABLE 3

| compounds | 50% growth inhibiting concentration (μM) | | Selective toxicity |
|---|---|---|---|
| | *Trypanosoma brucei rhod.* | Cytotoxicity L6 | |
| A-1 | 0.016 | 30 | 1900 |
| A-4 | 0.41 | 76 | 190 |
| A-6 | 0.13 | 44 | 340 |
| A-8 | 0.30 | 1.8 | 6.0 |
| A-9 | 0.14 | 8.1 | 58 |
| A-10 | 0.20 | 20 | 100 |
| A-12 | 0.90 | 17 | 19 |
| A-13 | 0.11 | 13 | 120 |
| A-14 | 0.041 | 9.1 | 220 |
| A-15 | 0.089 | 22 | 250 |
| A-16 | 0.030 | 0.94 | 31 |
| A-17 | 0.093 | 53 | 570 |
| melarsoprol | 0.006 | 7.8 | 1300 |

The compounds of the present invention showed a similar growth inhibition effect on African trypanosome as the existing drug, melarsoprol. Moreover, they showed toxicity weaker than or similar to existent drugs against normal cells. Therefore, it can be estimated to be effective as an anti-African trypanosome (African sleeping disease) agent with less side-effect. Moreover, as these compounds of the invention do not contain arsenical atoms in the molecule, it will not have serious side-effects as arsenic poisoning to patients.

Example 4

4-1. Culture of American Trypanosoma Protozoa

In the present example, amastigote and trypomastigote infected with rat L6 cells of protozoa of *Trypanosoma cruzi* (Tulahuen C2C4 strain) were used. As medium used in the test, RPMI 1640 medium containing L6 cells was supplemented so that L-glutamine (200 mM) becomes 1%, fetal bovine serum becomes 10%, which was cultured under $CO_2$ concentration 5%, at 37° C.

4-2. American Trypanosome Protozoa Growth Inhibition Screening Test

The compounds of the present invention to be used in the test and the positive target agent (benznidazole) were dissolved in DMSO to make a test solution of a predetermined concentration. A medium containing $5×10^3$ protozoa was added to wells of a 96-well culture plate, and pre-cultured for 48 hours. After replacing the medium, test solution containing drug of a predetermined concentration or a drug-free DMSO was added. Test solutions were taken by duplicates. After culturing the culture plate in an incubator for 96 hours, growth inhibition activity was tested. Test was conducted as follows.

50 μL of CPRG/Nonidet was added to each well, and allowed to rest for 2 to 6 hours. Next, the culture plate was placed on a fluorescent micro-plate reader, and the absorbance was measured at 540 nm. Growth inhibition rate was calculated with the following formula based on the protozoan infection rate which was obtained by calculating trypanosome infection rate of the test solution added group and control group, to obtain a 50% growth inhibition concentration ($EC_{50}$).

Growth inhibition rate (%)=$\{1-(b-a)/(c-a)\} \times 100$ a: early infection rate
b: infection rate when test solution was added
c: infection rate of the control 4-3. Determination of Drug Efficacy of American Trypanosome Chemotherapy index used as an index of selective toxicity against American trypanosome protozoa was calculated with the following formula, to determine drug efficacy.

Chemotherapy index=($EC_{50}$ value of a sample against rat $L6$ cells)/($EC_{50}$ value of a sample against American trypanosome protozoa)

$EC_{50}$ values of samples of the compounds of the present invention and the positive target drug against American trypanosome protozoa and rat L6 cells, as well as selective toxicity index are shown in Table 4.

TABLE 4

| compounds | 50% growth inhibition concentration (μM) | | Selective toxicity |
|---|---|---|---|
| | *Trypanosoma cruzi* | Cytotoxicity L6 | |
| A-1 | 5.1 | 30 | 5.9 |
| A-8 | 0.99 | 1.8 | 1.8 |
| A-9 | 4.1 | 8.1 | 2.0 |
| A-10 | 0.16 | 20 | 130 |
| A-14 | 1.2 | 9.1 | 7.6 |
| A-15 | 0.98 | 22 | 22 |
| A-16 | 0.090 | 0.94 | 10 |
| benznidazol | 0.87 | — | — |

The compounds of the present invention showed a similar growth inhibiting effect on American trypanosome as the existing drug, benznidasol. Moreover, they showed weak toxicity against normal cells. Therefore, it can be estimated to be effective as an anti-American trypanosome (Chaga's disease) agent with less side-effect.

Example 5

5-1. Culture of Leishmaniasis Protozoa

In the present example, *Leishmania donovani* (MHOM/ET/67/L82 strain) was used. Protozoa was subcultured in Syrian Golden hamster, from which an amastigote was obtained. In the experiment, SM medium supplemented with 10% heat-treated bovine fetal serum was used, which was adjusted to pH 5.4, and cultured in an atmosphere of 5% $CO_2$ concentration, at 37° C.

5-2. *Leishmania* Protozoa Growth Inhibition Screening Test

The compounds of the present invention to be used in the present test and the positive target drug (miltefosine) were dissolved in DMSO to make a test solution of a predetermined concentration. After adding a medium containing a predetermined number of protozoa to wells of a 96-well culture plate and pre-treating, concentration of the amastigote was measured with CASY cell analysis system (Scharfe, Germany). Then, test solution containing a drug of a predetermined concentration or a drug-free DMSO was added. Test solutions were taken by duplicates. After culturing the culture plate for 72 hours in an incubator, growth inhibition activity was tested. Test was conducted as follows.

10 μL of Alamar Blue aqueous solution was added to each well, and the resultant was further cultured for 2 hours. Next, the culture plate was placed on a fluorescent micro-plate reader (Spectramax Gemeni XS; US Molecular Device), radiated at an excited wavelength of 536 nm. Fluorescent intensity was measured at 588 nm, and infection rate of leishmania protozoa of the test solution added-group and control was calculated, to obtain a 50% growth inhibition concentration ($EC_{50}$).

Growth inhibition rate (%)=$\{1-(b-a)/(c-a)\} \times 100$ a: early infection rate
b: infection rate when test solution was added
c: infection rate of the control 5-3. Determination of Drug Efficacy of Leishmania Chemotherapy index used as an index of selective toxicity against leishmania protozoa was calculated with the following formula, to determine drug efficacy.

Chemotherapy index=($EC_{50}$ value of a sample against rat $L6$ cells)/($EC_{50}$ value of a sample against leishmania protozoa)

$EC_{50}$ values of samples of the compounds of the present invention and the positive target drug against leishmania protozoa and rat L6 cells, as well as selective toxicity index are shown in Table 5.

TABLE 5

| compounds | 50% growth inhibition concentration (μM) | | Selective toxicity |
|---|---|---|---|
| | *Leishmania donovani* | Cytotoxicity L6 | |
| A-1 | 0.0083 | 30 | 3600 |
| A-8 | 0.056 | 1.8 | 32 |
| A-9 | 0.023 | 8.1 | 350 |
| A-10 | 0.15 | 20 | 130 |
| A-13 | 0.047 | 13 | 280 |
| A-14 | 0.20 | 9.1 | 46 |
| A-15 | 0.17 | 22 | 130 |
| A-16 | 0.0080 | 0.94 | 120 |
| A-17 | 0.011 | 53 | 4800 |
| miltefosine | 0.28 | — | — |

The compounds of the present invention showed a similar growth inhibition effect on leishmania protozoa as the existing drug, miltefosine. Further, toxicity against normal cells was also weak. Therefore, it can be estimated to be effective as an anti-leishmania agent with less side-effect.

From the results of Examples 1 to 5, it has been clarified that the compounds of the present invention show a growth inhibition effect against parasitic protozoan infection even when a low dosage is administered, and do not damage mammal cells even when administrating a dosage higher than that showing protozoan growth inhibition. In other words, from the above results, it has been clarified that the compounds of the present invention are suitable as drugs preventing or treating parasitic protozoan infections.

INDUSTRIAL APPLICABILITY

According to the present invention, a medicinal composition for preventing or treating parasitic protozoan infections, having a high selective toxicity against parasitic protozoan infection, and a superior preventive or treating effect can be provided.

The invention claimed is:

1. A method of treating parasitic protozoan infections comprising administering a pharmaceutically effective amount of a compound shown by the following general formula (1) as an active ingredient

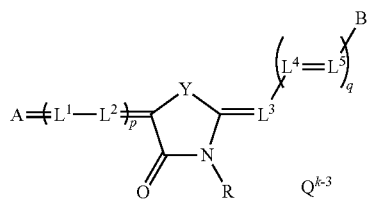

(1)

wherein R represents an alkyl or aryl group;
A and B each independently represents a heterocyclic ring selected from the group consisting of a thiazolyl, benzothiazolyl, and naphtothiazolyl, wherein the heterocyclic ring optionally has one or more alkyl substituents, wherein a nitrogen atom in the thiazole ring of B has a positive charge;
Y represents S;
$L^1$, $L^2$, $L^3$, $L^4$ and $L^5$ each independently represents a methine group
Q represents a physiologically acceptable anion; k represents an integer of 0 to 2, necessary to make the electric charge of the whole molecule 0;
p is 1 and q is 0,
wherein the parasitic protozoan infection is malaria, African trypanosomiasis, or American trypanosomiasis.

2. The method of treating parasitic protozoan infections according to claim 1, wherein the compound is selected from

A-1

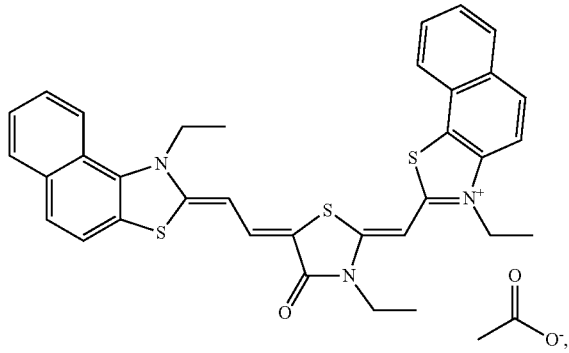

A-2

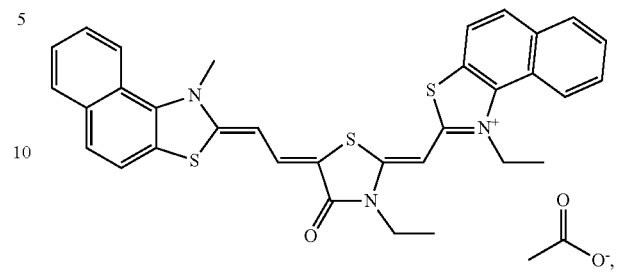

A-3

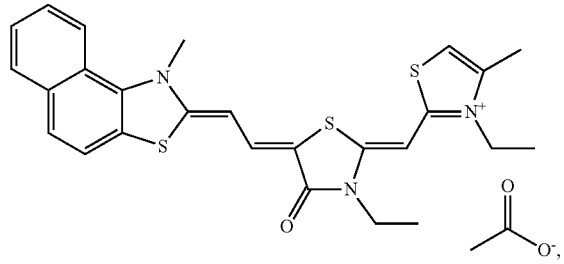

and

A-15

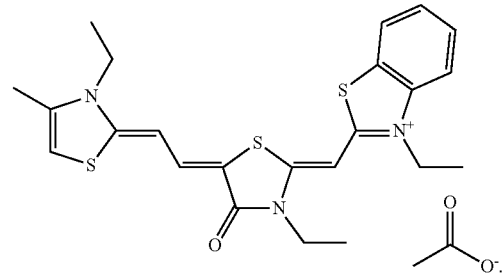

3. The method of treating parasitic protozoan infections according to claim 1, wherein Q is halogen ion, sulfonate ion, or carboxylate ion.

* * * * *